(12) United States Patent
Ahlstrand

(10) Patent No.: US 6,293,933 B1
(45) Date of Patent: *Sep. 25, 2001

(54) DIAPER

(75) Inventor: Ove Ahlstrand, Älvkarleby (SE)

(73) Assignee: Marlene Sandberg AB, Saltsjo Duvnas (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/817,471

(22) PCT Filed: Oct. 18, 1995

(86) PCT No.: PCT/SE95/01222

§ 371 Date: Jun. 6, 1997

§ 102(e) Date: Jun. 6, 1997

(87) PCT Pub. No.: WO96/12457

PCT Pub. Date: May 2, 1996

(30) Foreign Application Priority Data

Oct. 19, 1994 (SE) .................................................... 9403577

(51) Int. Cl.$^7$ .................................................. A61F 13/46
(52) U.S. Cl. .................................. 604/385.101; 604/378; 604/380; 604/381; 604/382
(58) Field of Search .................................. 604/378, 380, 604/381, 382, 385.1, 385.101, 385.01

(56) References Cited

U.S. PATENT DOCUMENTS

| | | | |
|---|---|---|---|
| 3,430,629 | * 3/1969 | Murphy | 604/381 |
| 3,559,649 | * 2/1971 | Grad | 604/382 |
| 3,693,622 | * 9/1972 | Jones | 604/381 |
| 3,763,502 | * 10/1973 | Lauman | 604/381 |
| 4,184,498 | * 1/1980 | Franco | 128/290 |
| 4,503,098 | * 3/1985 | Potts | 604/381 |
| 4,592,751 | * 6/1986 | Gegleys | 604/380 |
| 4,678,464 | * 7/1987 | Holtman | 604/385 |
| 4,753,644 | * 6/1988 | Cottenden et al. | 604/378 |
| 4,892,535 | 1/1990 | Bjornberg et al. | |
| 5,300,053 | 4/1994 | Genaro | |
| 5,308,344 | * 5/1994 | Toth | 604/382 |
| 5,451,442 | * 9/1995 | Pienick et al. | 604/380 |
| 5,743,776 | * 4/1998 | Igaue et al. | 604/381 |

FOREIGN PATENT DOCUMENTS

| | | |
|---|---|---|
| 3 426 897 | 1/1986 | (DE) . |
| 400 459 | 4/1974 | (SE) . |

* cited by examiner

Primary Examiner—John G. Weiss
Assistant Examiner—Michael Bogart
(74) Attorney, Agent, or Firm—Ware, Fressola, Van der Sluys & Adolphson LLP

(57) ABSTRACT

The invention relates to a diaper of the kind including outer and inner layers enclosing an absorbing layer, an absorbing body or the like, wherein at least one recess is arranged in the absorbing layer and a liquid passage in line with said recess at the inner covering layer. In addition to the recess in the absorbing layer, there are a number of channels extending from the recess forming together with the recess a storage space defined by the outer and inner layers of the diaper for temporary receiving liquid not yet absorbed and providing an extended liquid absorbing edge surface.

11 Claims, 3 Drawing Sheets

DIAPER

BACKGROUND OF THE INVENTION

1. Technical Field

This invention relates to diapers especially for infants, but also for incontinence protection and napkins and more in details to the type of diapers including at least one at least partly moisture tight enclosing layer and one or more inner layers having a good absorption ability.

2. Description of the Prior Art

There are known different ways of controlling the absorption of liquid in the absorbing layer.

SE 400 459 discloses a disposable diaper wherein an absorbing layer is provided with a number of through openings. The absorbing layer is freely arranged relating to a tight rear or outside layer and is covered by a moisture permeable inner or forward layer. The idea with this is that moisture will be able to pass through the inner layer simultaneously as it is partly absorbed, pass through the through openings towards the rear of the absorbing layer in order to, aided by the tight outside layer, be distributed or spread over the absorbing layer.

DE3 426 897 discloses another solution of a similar kind. It includes a tight outer or rear layer, an absorbing filling and an inner layer and also in this case the absorbing layer is provided with one or more through openings. The inwardly facing covering layer is double and includes a first tight layer having holes corresponding to those of the absorbing layer and an outer layer of non-woven material. The intention hereby is to gain the advantage that liquid can be spread on the non-woven material in order to eventually reach the position of any of the openings and pass through the non-woven material and through any of the holes in the tight foil layer to reach the openings of the absorbing layer so that the moisture can be absorbed essentially through the edges of the latter openings.

Common features of the known constructions are that they, in spite of the increase of the absorption area by the holes or openings provided and the passages arranged at the inner layer, are unable to take care in a desired and intended way, of concentrated volumes of liquid within a limited area, the result being that the liquid is distributed over the entire inside of the diaper and easily leaks out at the edges. It also occurs that liquid in free state fills one or any of the openings of the absorbing layer and to oversaturation fills the adjoining absorption material portions whereas the rest of the absorbing layer is unutilized and only eventually will take in the absorption. Local oversaturation of the absorbing layer will result in leak risks back towards the carrier or laterally at the edges.

It has been established that, in known constructions, the absorbing ability of the absorbing material is poorly taken advantage of. An estimation discloses that only about half of the material is used which means that half of it is disposed of unused. One reason behind the faulty effect seems to be that once the material absorbs liquid, it has a tendency to compact and form clods and this prevents the liquid from spreading. One reason behind this tendency to form lumps or clods is that the material consists of long and short fibers. The movements of the user result in separation of the fiber material so that the continuous layer or body of fiber material disintegrates into smaller gatherings or lumps of fibers. The gaps or cracks formed between the separate gatherings or lumps make the intended distribution of liquid over the entire absorbing layer or body impossible, which results in local oversaturation and leaking in spite of the fact that only a fraction of the capacity of the material has been taken advantage of.

OBJECTS OF THE INVENTION

One essential object of the invention is to bring about a diaper or the like which is so arranged that it has an improved ability to absorb and keep liquid and moisture without leaking and in more detail, a diaper where the absorbing material is utilized to a high degree in order to reach this high absorption ability.

Another object of the invention is to conceive a diaper having the ability to temporarily store liquid in free state before its absorption.

Another object is to improve the function of a diaper by keeping the absorption material in its place.

One more object is to minimize the leak risk resulting from local oversaturation of the absorption material.

Still another object is to increase the absorption area without reducing the total absorption capacity, establish a quicker absorption with a reduced amount of absorption material and reduce the cost.

As a result of the reduced amount of absorbing material, the demand to use biodegradable, i.e. compostable, material at a price not exceeding the current price of diapers is met.

A final object is also to bring about a diaper comfortable to wear and which presents a dry inner face towards the user after having absorbed liquid.

SUMMARY OF THE INVENTION

It has now been found that the foregoing and related objects can be readily attained in a diaper or the like hygienic product comprising:

(a) an outer layer essentially impermeable to liquid;

(b) an absorption body adjacent the outer layer, the absorption body having a thickness and defining at least one recess, the absorption body defining a plurality of channels extending from an edge of the at least one recess in different directions, the channels extending from the edge of the at least one recess towards an outer edge of the absorption body, the at least one recess and the channels extending therefrom have a depth corresponding to at least part of the thickness of the absorption body; and (c) a layer permeable to liquid secured to the outer layer at least in a position chosen from the group consisting of the at least one recess, the channels and the at least one recess and channels thereby stabilizing the absorption body.

Desirably, the diaper or the like hygienic product further comprises an inner layer at least partially permeable to liquid inwardly adjacent the absorption body and the permeable layer secured to the outer layer, the absorption body being between the inner and outer layers. The absorption body defines the at least one recess at a permeable portion of the inner layer. The channels together with the at least one recess form, between the outer and inner layers, a defined storage space for temporary storing of liquid in free state awaiting absorption.

In yet another feature of the invention, the inner layer presents a portion permeable to liquid in an area essentially corresponding with the area of the at least one recess of the absorption body and areas impermeable to liquid covering at least a portion of at least some of the channels extending from the at least one recess.

The invention will be fully understood when reference is made to the following detailed description taken in conjunction with the accompanying drawings.

BRIEF DESCRIPTION OF THE DRAWINGS

The invention will be described in the following with references to the attached drawings, in which FIG. 1 diagramatically illustrates the course of events on discharge of a volume of liquid in a diaper or the like having an absorbing layer.

DETAILED DESCRIPTION OF THE INVENTION

Figure 1:
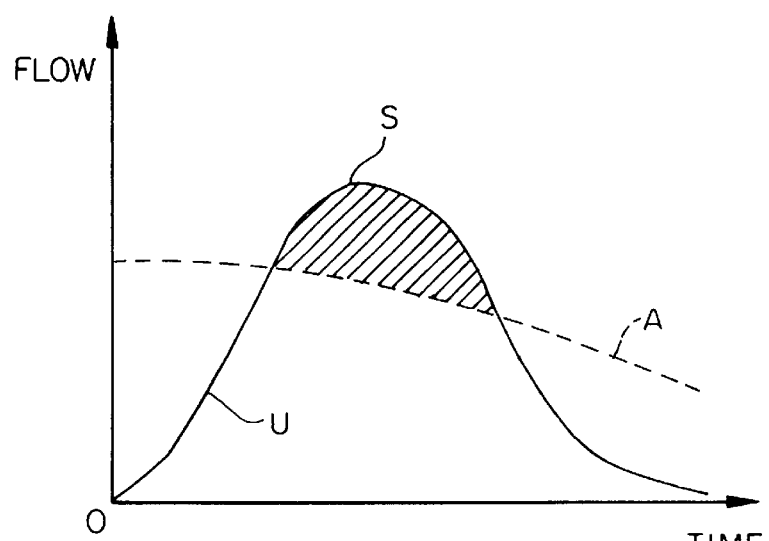

Time is indicated along the X axis and the magnitude of the flow along the Y axis. The flow of liquid is indicated by the curve U commencing at 0 whereas the ability to absorb is marked by the dash line A. During an initial period of time the liquid will be fully absorbed but upon increase of the flow beyond a certain amount there occurs an excess, the hatched area S representing a volume of liquid in free state on the surface of an absorbing layer or body. As the flow eventually decreases the absorbing material is again able to take care of and absorb the liquid as can be seen at the right hand part of the curve U.

A basic problem hitherto not solved is to arrange for temporary storage of the partial volume which cannot be taken care of immediately and prevent it from leaking out laterally or otherwise along the diaper.

According to this invention there is in the absorbing layer or body 1, preferably at the center thereof arranged at least one slightly elongated recess 2 from the edges of which narrow branch channels 3 extend in different directions outwardly from the recess 2.

Further, there is, on the outer face of the absorbing layer 1, arranged an essentially moisture and/or liquid proof layer 4, which can be a separate barrier layer outside or include a coating in an appropriate way attached to an outer layer or lining of non-woven material or the like provided at the absorbing layer. On the opposite or inner side of the absorbing layer there is a layer or lining 5 which is permeable for liquid at least in an area or areas localized essentially in line with the at least one recess 2 in the absorption layer 1, said layer or lining also being constituted by non-woven material or the like.

Figure 2:
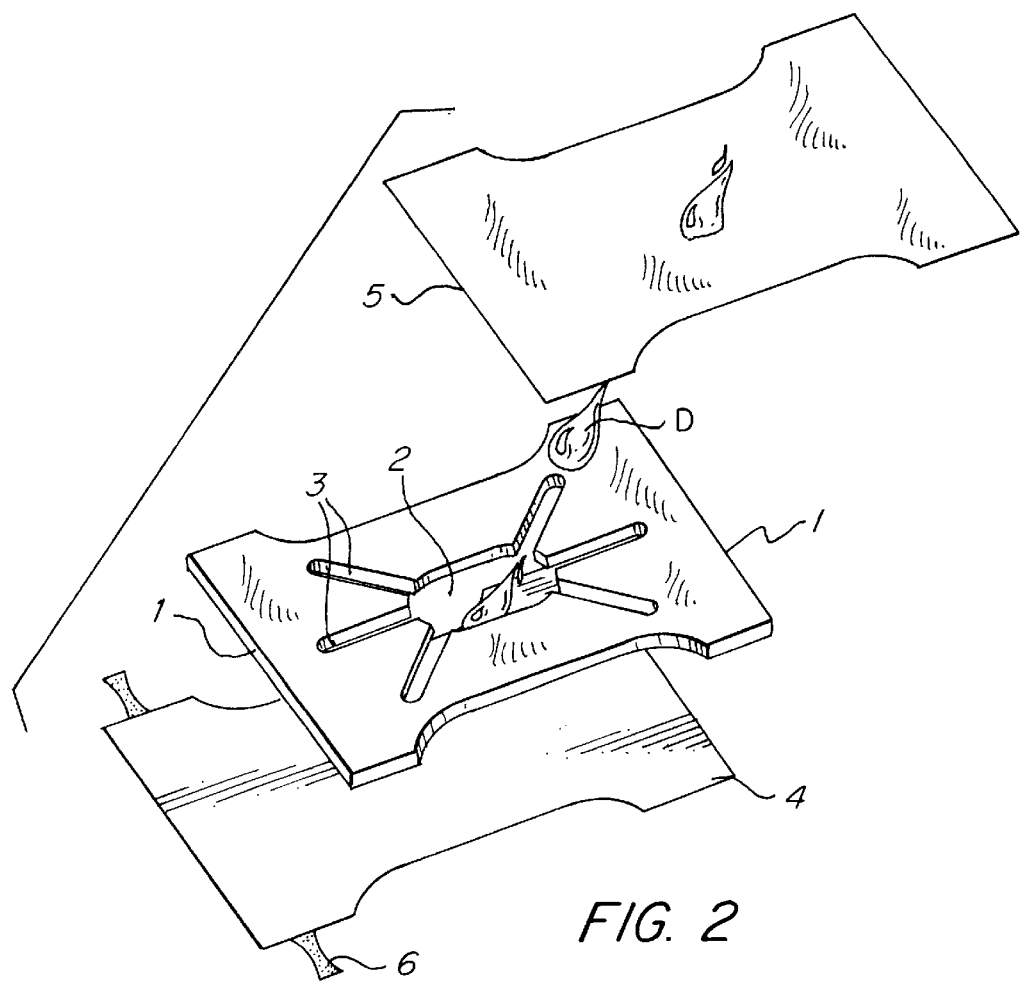
FIG. 2 is an exploded perspective view showing the components included in a first embodiment of a diaper according to the invention, FIG. 3 in the same way as FIG. 2 shows the components included in a modified embodiment of the diaper according to the invention, FIG. 4 in the same way as FIGS. 2 and 3 shows the components included in a preferred embodiment of the diaper according to the invention.
Figure 3:
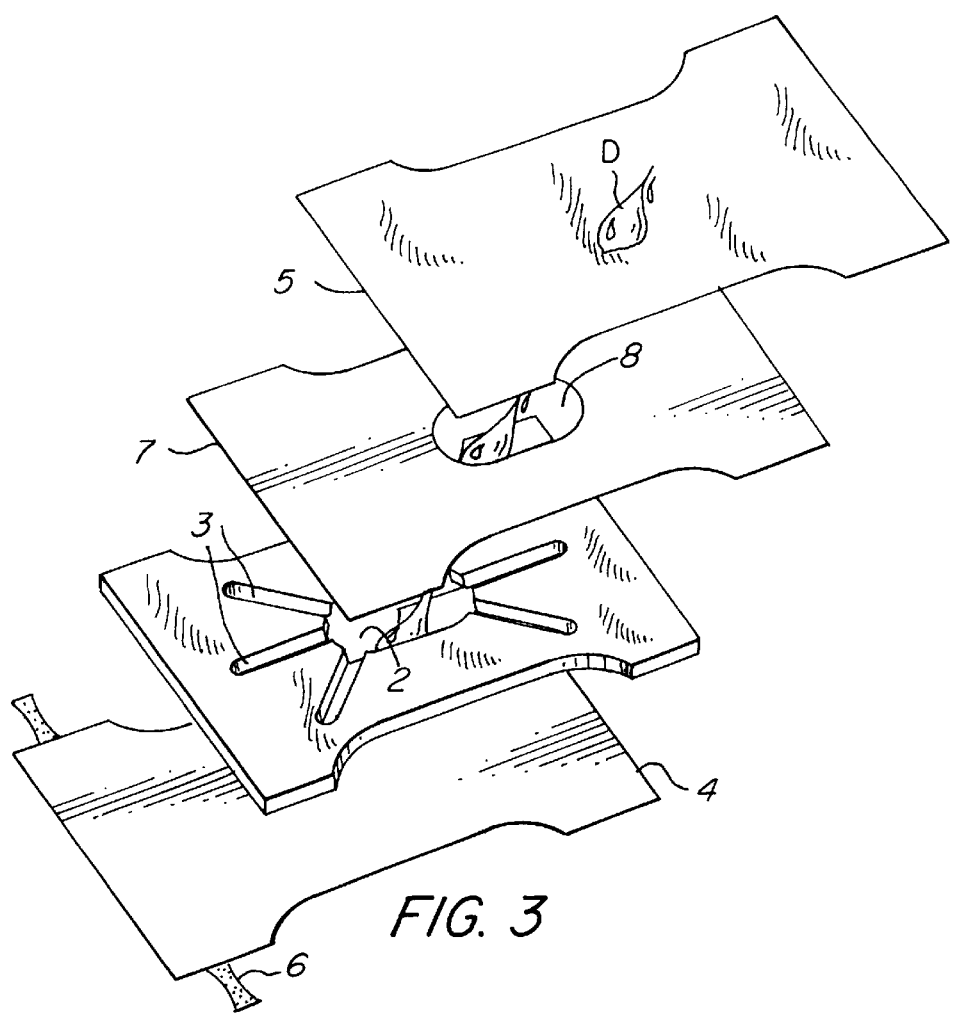
Figure 4:
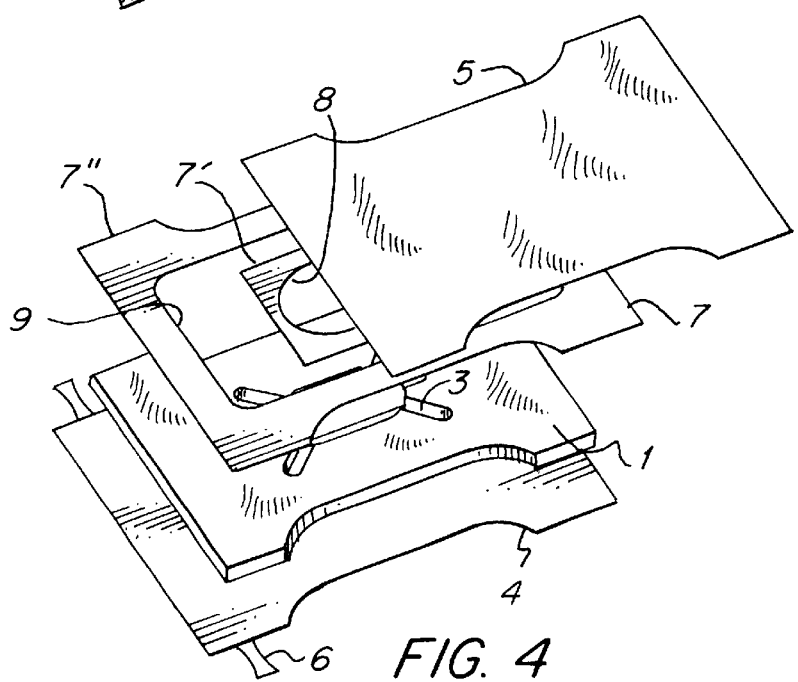

In FIGS. 2–4, a drop D illustrates a volume of liquid to be caught by the diaper. FIG. 2 shows how the volume of liquid can pass through the permeable portion of the inner layer or lining 5 and be caught in the recess 2.

After having joined the different layers along their edges, the outer layer 4 will form a tight bottom for the recess 2 simultaneously as the inner layer 5 forms a permeable cover over the same. By arranging the elongated recess 2 with the channels 3 branching out from it, a trapping area and cavity having an extremely long edge length is created. The total length of the edges defining the recess 2 and the channels 3, respectively, form an efficient absorption surface and the extension thereof is decisive for the absorption ability and speed. Free liquid entering the recess 2 and flowing out therein and into the branch channels 3 will meet a very long contact surface which facilitates and speeds up the absorption. The increase of absorption area gained by arranging the branch channels 3, is decisive for the ability to store, i.e. the ability to temporarily take care of an excess of arriving liquid not immediately absorbable.

At conventional circular recesses or openings made in the absorbing layer, the area of absorption is equal to the face of the edge defining the recess. An addition of liquid filling the recess can be absorbed only as fast as the material adjoining the recess manages to forward and take care of the liquid. The excess liquid normally distributes itself over the face of the diaper and seeps out at the edges. By combining the recess with channels or branches extending therefrom, the edge surface ensuring the absorption will be multiplied and also the speed of absorption. An arriving volume of liquid will be distributed and quickly absorbed over a large area. A similar effect cannot be reached by arranging several recesses close to each other, as there is no communication between the recesses and excess amounts of liquid will have to flow along the surface of the diaper in order to reach one hole or the other close by.

Scattered or detached holes or recesses lack the ability to distribute the liquid over larger areas, whereas the combination of recess and channels suggested now can ensure utilization of the entire volume of absorbing material.

In the embodiment according to FIG. 2, there is a non-woven type inner layer 5 with or without moisture penetration preventing cover. The outer layer 4 may also be of non-woven type but has a cover or layer preventing moisture penetration. At the layer 4, there are strips of adhesive tape or the like 6 for the fastening of the diaper.

In the embodiment according to FIG. 3, the single inner layer 5 is completed with a barrier layer 7 forming a moisture barrier inside the non-woven layer 5. In the area adjacent the recess 2 of the absorption layer 1, there is an opening 8 having essentially the same area as the recess 2. A flow of liquid meeting the inner layer 5 at the recess 2 thus can pass directly into the recess 2. Each of the branch channels 3 covered by the barrier layer 7 forms an inwardly and outwardly covered pocket opening into the recess and in such chambers excess volumes may be temporarily stored until absorption takes place without any leak risk.

At some distance from the position of the recess 2 and the opening 8, respectively, in the embodiment according to FIG. 4, there is an additional preferrably annular area permeable to liquid in order to prevent some liquid reaching the inner layer 5 remote from the opening 8 from flowing out and possibly leaking out at the edges of the diaper. In FIG. 4, it can be seen how the barrier layer 7, which can be constituted by a coating on the non-woven layer 5, is provided with an outer surrounding opening 9 in addition to the opening 8. The inner barrier layer portion 7' around the opening 9 ensures the storing function of the storing channels 3 and an outer barrier layer portion 7" covering the area along the edge of the diaper and prevents squeezing out of liquid there. The surrounding opening 9 may naturally be replaced by several smaller openings arranged essentially in the same way.

The embodiment according to FIG. 4 results not only in an efficient trapping of volumes of liquid entering the intended central area around the recess 2 but also liquid which—e.g. because of displacement of the diaper—meets the surface remote from the recess. In such cases, the ability to temporarily store free liquid will be reduced as only the outer ends of the channels 3 and not the recess 2 will be reached immediately. This drawback is, however, clearly compensated by the increased general ability to catch liquid also outside the normally intended area.

Figure 5:
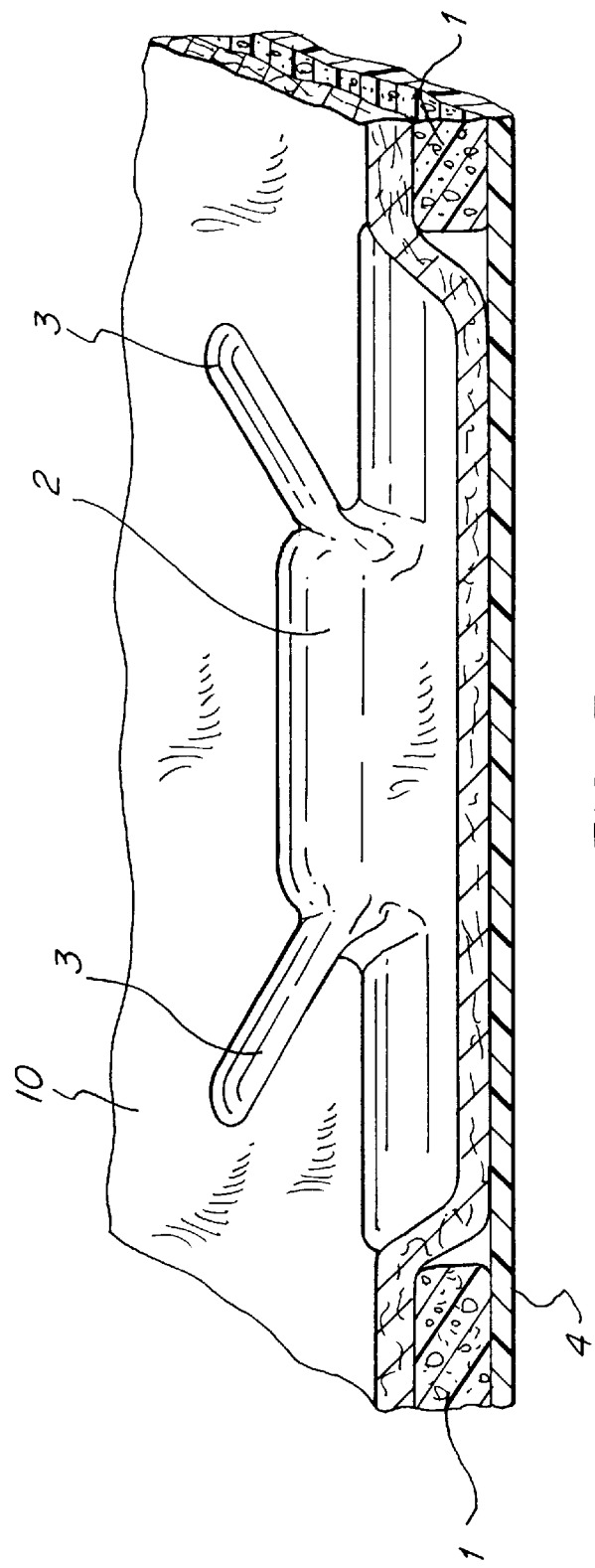
FIG. 5 is a perspective cross-sectional view of a portion of any one of the embodiments of the diaper of FIGS. 2–4 with the inner layers removed to show the position of an additional liquid permeable layer secured to the outer liquid impermeable layer at the recess and/or the channels and stabilizing the absorption material of the absorption layer or body.

In each of the embodiments of FIGS. 2–4, a liquid permeable layer 10 (FIG. 5) of non-woven material or the like can be between the layer or lining 5 and the absorption layer or body 1. As shown in FIG. 5, the liquid permeable layer is secured to the outer liquid impermeable layer at the recess 2 and/or the channels 3 and stabilizes the absorption material of the absorption layer or body 1.

The diaper arranged according to the invention is preferably manufactured by biologically degradeable material. Thus, the non-woven layers may be manufactured by viscose material, the absorbing layer as before by cellulose products and the barrier layers or covers by wax products on a natural basis or by other biodegradeable barrier materials available on the market.

What is claimed is:

1. Diaper or the like hygienic product comprising:
   (a) an outer layer essentially impermeable to liquid;
   (b) an absorption body adjacent the outer layer, the absorption body having a thickness and defining at least one recess, the absorption body defining a plurality of channels extending from an edge of the at least one recess in different directions, the channels extending from the edge of the at least one recess towards an outer edge of the absorption body, the at least one recess and the channels extending therefrom have a depth corresponding to at least part of the thickness of the absorption body;
   (c) a layer permeable to liquid secured to the outer layer at least in a position chosen from the group consisting of the at least one recess, the channels and the at least one recess and channels thereby stabilizing the absorption body; and
   (d) an inner layer at least partially permeable to liquid inwardly adjacent the absorption body and the permeable layer secured to the outer layer, the absorption body being between the inner and outer layers, the absorption body defining the at least one recess at a permeable portion of the inner layer, and the channels together with the at least one recess form, between the outer and inner layers, a defined storage space for temporary storing of liquid in free state awaiting absorption.

2. Diaper according to claim 1, wherein the inner and outer layers and the absorbing body are made of biologically degradable materials.

3. Diaper according to claim 2, wherein the inner and outer layers are made of a viscose material and the absorbing body is made of a cellulose material.

4. Diaper according to claim 1, wherein the absorbtion body is an absorption layer between the inner and outer layers.

5. Diaper according to claim 1, wherein the inner layer includes a liquid barrier layer having a liquid permeable area in a position opposite the recess of the absorption body.

6. Diaper according to claim wherein the liquid barrier layer further includes at least one additional liquid permeable area, forming liquid permeable zones remote from the liquid permeable area opposite the recess.

7. Diaper or the like hygienic product comprising:
   (a) an outer layer essentially impermeable to liquid;
   (b) an absorption body adjacent the outer layer, the absorption body having a thickness and defining at least one recess, the absorption body defining a plurality of channels extending from an edge of the at least one recess in different directions, the channels extending from the edge of the at least one recess towards an outer edge of the absorption body, the at least one recess and the channels extending therefrom have a depth corresponding to at least part of the thickness of the absorption body;
   (c) a layer permeable to liquid secured to the outer layer at least in a position chosen from the group consisting of the at least one recess, the channels and the at least one recess and channels thereby stabilizing the absorption body; and
   (d) an inner layer at least partially permeable to liquid inwardly adjacent the absorption body and the permeable layer secured to the outer layer, the absorption body being between the inner and outer layers, the absorption body defining the at least one recess at a permeable portion of the inner layer, and the channels together with the at least one recess form, between the outer and inner layers, a defined storage space for temporary storing of liquid in free state awaiting absorption, the inner layer presents a portion permeable to liquid in an area essentially corresponding with the area of the at least one recess of the absorption body and areas impermeable to liquid covering at least a portion of at least some of the channels extending from the at least one recess.

8. Diaper according to claim 7, wherein the areas impermeable to liquid covering at least a portion of at least some of the channels are provided by a liquid barrier layer having a liquid permeable area in a position opposite the recess of the absorption body.

9. Diaper according to claim 8, wherein the liquid barrier layer further includes at least one additional liquid permeable area, forming liquid permeable zones remote from the liquid permeable area opposite the recess.

10. Diaper according to claim 8, wherein the liquid barrier layer has a coating of biologically degradeable material.

11. Diaper according to claim 10, wherein the biologically degradeable material is a natural wax.

* * * * *

UNITED STATES PATENT AND TRADEMARK OFFICE
CERTIFICATE OF CORRECTION

PATENT NO. : 6,293,933 B1
DATED : September 25, 2001
INVENTOR(S) : Ove Ahlstrand It is certified that error appears in the above-identified patent and that said Letters Patent is hereby corrected as shown below:

<u>Title page, Item [54] and Column 1, line 1,</u>
The Title should be -- ABSORBENT ARTICLE WITH CHANNELS --.

<u>Column 4,</u>
Line 62, "9" should be -- 8 --.

<u>Column 6,</u>
Line 7, after "claim", -- 5 -- should be inserted.

Signed and Sealed this

Ninth Day of July, 2002

*Attest:*

*Attesting Officer*

JAMES E. ROGAN
*Director of the United States Patent and Trademark Office*